United States Patent [19]

Tang et al.

[11] Patent Number: 4,470,930
[45] Date of Patent: Sep. 11, 1984

[54] PREPARATION OF NUCLEAR CHLORINATED AROMATIC COMPOUNDS

[75] Inventors: David Y. Tang, Amherst; Byron R. Cotter, Grand Island, both of N.Y.; Frederick J. Goetz, Santa Ana, Calif.

[73] Assignee: Occidental Chemical Corporation, Niagara Falls, N.Y.

[21] Appl. No.: 347,390

[22] Filed: Feb. 9, 1982

[51] Int. Cl.³ .............. C07C 121/52; C07C 119/048; C07C 25/13
[52] U.S. Cl. .................. 260/465 G; 260/453 AR; 260/544 D; 568/656; 570/127
[58] Field of Search ....... 260/465 G, 453 AR, 544 D; 568/656; 570/127

[56] References Cited

U.S. PATENT DOCUMENTS 4,225,534  9/1980  Yoshikawa ................... 260/465 G

OTHER PUBLICATIONS

Vorozhtsov et al., Zhurnal Obshchei Khimii, Vol. 31, No. 4, pp. 1222–1226 (1961).

*Primary Examiner*—Dolph H. Torrence
*Attorney, Agent, or Firm*—James F. Tao; Arthur S. Cookfair

[57] ABSTRACT

Chloro-aromatic compounds of the formula

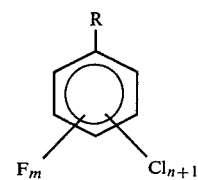

wherein R is $CF_3$, $OCF_3$, $OC_2F_5$, CN, NCO, or COCl, m is 0 or 1, and n is 0 or 1 are prepared by the vapor phase chloro-denitration reaction of a chlorinating agent with a nitro-aromatic compound of the formula

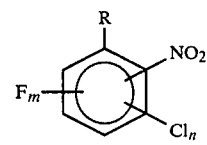

where R, m, and n are as defined above.

53 Claims, No Drawings

PREPARATION OF NUCLEAR CHLORINATED AROMATIC COMPOUNDS

BACKGROUND OF THE INVENTION AND PRIOR ART STATEMENT

This invention relates to a vapor-phase chloro-denitration process for the preparation of nuclear-chlorinated aromatic compounds useful as chemical intermediates.

The preparation of chlorobenzene compounds by chlorodenitration of the corresponding nitrobenzene compounds in the liquid phase is known. For example, the liquid phase chlorodenitration of 2-nitrobenzonitriles to form the corresponding 2-chlorobenzonitriles is disclosed in U.S. Pat. No. 4,225,534. Furthermore, it is known from the chemical literature that certain nitrobenzene or fluoronitrobenzene compounds may react with chlorine in the vapor phase with the replacement of nitro groups by chlorine atoms. (Vorozhtsov et al, Zhurnal Obshchei Khimii, Vol. 31, No. 4, pp. 1222–1226, April, 1961). Such vapor phase reactions have been shown to be feasible only with certain unsubstituted nitrobenzenes or fluoronitrobenzenes. However, it has not heretofore been known or suggested that other substituted nitrobenzenes or substituted fluoronitrobenzenes might undergo chlorodenitration by vapor phase reaction with chlorine. U.S. Pat. No. 4,259,510 discloses a process for the preparation of trifluoromethylphenyl nitrophenylethers utilizing phenol reactants which may be prepared from substituted halobenzene reactants, including dihalobenzotrifluorides. U.S. Pat. No. 4,012,453 discloses a catalyzed oxychlorofluorination reaction of toluene, benzotrichloride, hydrogen fluoride and oxygen wherein the reaction product includes chlorofluorobenzotrifluoride as a component thereof. In addition, the incidental preparation of a chlorofluorobenzotrifluoride is described in Feast et al in J. Chem. Soc. (c), 1971, 1547–49. The reference discloses 4-chloro-3-fluoro-benzotrifluoride as a minor co-product obtained during the synthesis of 3,4-difluorobenzotrifluoride from 3-amino-4-fluorobenzotrifluoride.

SUMMARY OF THE INVENTION

It has now been found that substituted chloroaromatic compounds of the formula

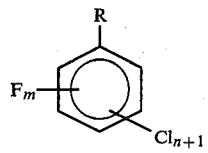

wherein m is 0 or 1, n is 0, 1 or 2, preferably 0 or 1 and R is $CF_3$, $OCF_3$, $OC_2F_5$, $CN$, $NCO$, or $COCl$, may be prepared by the vapor phase reaction of a chlorinating agent with a substituted nitro-aromatic compound of the formula

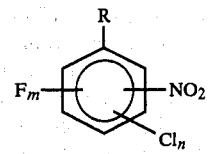

where m, n, and R are as defined above.

The chloro-denitration process of this invention is carried out under conditions of temperature and pressure appropriate for a vapor phase reaction, the exact conditions being dependent on the properties of the particular reactants employed. Typically, the process is carried out at atmospheric conditions and at a temperature in the range of about 250° to about 450° Celsius, or higher, preferably 290° to 410° C.

The proportions of reactants may vary widely with no critical limits. However, since chlorine is generally the less costly of the reactants, it is recommended to employ an excess thereof. For example, a molar ratio of $Cl_2$:organic of about 1.1:1 to about 10:1.

The process of the invention is useful for the preparation of various specific, ring fluorinated or unfluorinated mono-, di-, and tri-chloro-substituted benzotrifluorides, benzoyl chlorides, phenyl isocyanates, and benzonitriles, trifluoromethoxy-benzenes, and pentafluoroethoxybenzenes.

Typical of the chloro-substituted benzotrifluorides that may be prepared by the chloro-denitration process of this invention are 2-chlorobenzotrifluoride; 3-chlorobenzotrifluoride; 4-chlorobenzotrifluoride; 3-chloro-4-fluorobenzotrifluoride; 4-chloro-3-fluorobenzotrifluoride; 2-chloro-5-fluorobenzotrifluoride; 5-chloro-2-fluorobenzotrifluoride; 2-chloro-4-fluorobenzotrifluoride; 4-chloro-2-fluorobenzotrifluoride; 3-chloro-5-fluorobenzotrifluoride; 2,5-dichloro-4-fluorobenzotrifluoride; 4,5-dichloro-2-fluorobenzotrifluoride; 3,5-dichloro-4-fluorobenzotrifluoride; and the like. Typical of the chloro-substituted benzoyl chlorides that may be prepared are 2-chlorobenzoyl chloride; 3-chlorobenzoyl chloride; 4-chlorobenzoyl chloride; 4-chloro-3-fluorobenzoyl chloride; 3-chloro-4-fluorobenzoyl chloride; 2-chloro-4-fluorobenzoyl chloride; 4-chloro-2-fluorobenzoyl chloride; 2-chloro-5-fluorobenzoyl chloride; 5-chloro-2-fluorobenzoyl chloride; 3-chloro-5-fluorobenzoyl chloride; 2,5-dichloro-4-fluorobenzoyl chloride; 3,5-dichloro-4-fluorobenzoyl chloride; 4,5-dichloro-2-fluorobenzoyl chloride; and the like. Typical of the chloro-substituted trifluoromethoxybenzenes that may be prepared are 2-chlorotrifluoromethoxybenzene; 3-chlorotrifluoromethoxybenzene; 4-chlorotrifluoromethoxybenzene; 3-chloro-4-fluorotrifluoromethoxybenzene; 4-chloro-3-fluorotrifluoromethoxybenzene; 2-chloro-4-fluorotrifluoromethoxybenzene; 4-chloro-2-fluorotrifluoromethoxybenzene; 2-chloro-5-fluorotrifluoromethoxybenzene; 5-chloro-2-fluorotrifluoromethoxybenzene; 3-chloro-5-fluorotrifluoromethoxybenzene; 2,5-dichloro-4-fluorotrifluoromethoxybenzene; 4,5-dichloro-2-fluorotrifluoromethoxybenzene; 3,5-dichloro-4-fluoromethoxybenzene; and the like. Typical chloro-substituted pentafluoroethoxybenzenes that may be prepared are 2-chloro-pentafluoroethoxybenzene; 3-chloro-pentafluoroethoxybenzene; 4-chloro-pentafluoroethoxybenzene; 2-chloro-5-fluoro-pentafluoroethoxybenzene; 5-chloro-2-fluoro-pentafluoroethoxybenzene; 3-chloro-4-fluoro-pentafluoroethoxybenzene; 4-chloro-3-fluoropentafluoroethoxybenzene; 2-chloro-4-fluoro-pentafluoroethoxybenzene; 4-chloro-2-fluoro-pentafluoroethoxybenzene; 3-chloro-5-fluoro-pentafluoroethoxybenzene; 2,5-dichloro-4-fluoro-pentafluoroethoxybenzene; 4,5-dichloro-2-fluoro-pentafluoroethoxybenzene; 3,5-dichloro-4-fluoro-pentafluoroethoxybenzene; and the like. Typical chloro-substituted benzonitriles that may be prepared are 2-chlorobenzonitrile; 3-chlorobenzonitrile; 4-chlorobenzonitrile; 2-chloro-5-fluorobenzonitrile; 5-chloro-2-fluorobenzonitrile; 3-chloro-4-fluorobenzonitrile; 4-chloro-3-fluorobenzonitrile; 2-chloro-4-fluorobenzonitrile; 4-chloro-2-fluorobenzonitrile; 3-chloro-5-fluorobenzonitrile; 2,5-dichloro-4-fluorobenzonitrile; 4,5-dichloro-2-fluorobenzonitrile; 3,5-dichloro-4-fluorobenzonitrile; and the like. Typical chloro-substituted phenyl isocyanates that may be prepared are 2-chlorophenyl isocyanate; 3-chlorophenyl isocyanate; 4-chlorophenyl isocyanate; 2-chloro-5-fluorophenyl isocyanate; 5-chloro-2-fluorophenyl isocyanate; 3-chloro-4-fluorophenyl isocyanate; 4-chloro-3-fluorophenyl isocyanate; 2-chloro-4-fluorophenyl isocyanate; 4-chloro-2-fluorophenyl isocyanate; 3-chloro-5-fluorophenylisocyanate; 2,5-dichloro-4-fluorophenyl isocyanate; 4,5-dichloro-2-fluorophenyl isocyanate; 3,5-dichloro-4-fluorophenyl isocyanate; and the like.

The process of the invention is particularly useful for the preparation of a wide variety of specific useful chemical intermediates in substantially pure form, heretofore unavailable to the chemical industry. The chlorofluoro-aromatic compounds, prepared by the process of this invention are particularly useful for various organic syntheses based on nucleophilic substitution at the fluorine site. Thus, for example, the novel compound 5-chloro-2-fluorobenzotrifluoride may be reacted with an alkali metal hydroxide, such as potassium hydroxide, to produce 4-chloro-2-trifluoromethylphenol. Similarly, 2-chloro-4-trifluoromethylphenol, may be prepared by reaction of 3-chloro-4-fluorobenzotrifluoride with an alkali metal hydroxide, such as potassium hydroxide. Because of the higher reactivity of the nuclear fluorine, the reaction utilizing these novel chloro-fluorobenzotrifluoride reactants can be run under mild conditions to afford a high yield of the desired product with little or no formation of undesired isomers. The resultant chloro-trifluoromethylphenolate may be acidified to form the corresponding phenol compound. One method for the preparation of such compounds, as well as their use in the further preparation of various diphenylether herbicides is disclosed in detail in U.S. Pat. Nos. 4,262,152 and 4,259,510.

This novel compound 2,5-dichloro-4-fluorobenzotrifluoride may be reacted with hydroquinone, or a substituted phenol under basic conditions to form a phenyl ether of the type disclosed in U.S. Pat. No. 4,200,587 (compound V, Col. 4). As disclosed therein, such phenyl ethers may be further reacted with a suitable oxime to form useful herbicides.

The novel compound 2-chloro-5-fluorobenzotrifluoride may be similarly reacted with potassium hydroxide to produce the 4-chloro-3-trifluoromethylphenolate which may then be acidified to form the corresponding phenol compound. Upon hydrogenolysis, the 4-chloro-3-trifluoromethylphenol may be converted to 3-trifluoro-methylphenol. The use of this compound in the further preparation of pharmaceuticals is disclosed in detail in U.S. Pat. Nos. 4,168,388 and 4,018,895.

The following specific examples are provided to further illustrate this invention and the manner in which it may be carried out. It will be understood, however, that the specific details given in the examples have been chosen for purpose of illustration and are not to be construed as a limitation of the invention. In the examples, unless otherwise indicated, all parts and percentages are by weight and all temperatures are in degrees Celsius.

EXAMPLE 1

A solution of 5.3 parts of 2-nitrobenzonitrile in 37 parts of chloroform was introduced concurrently with chlorine at a $Cl_2$:nitrobenzonitrile molar ratio of 10:1 into a vapor phase reactor at a temperature of 390°–400° C. The reaction product was condensed, and collected. Analysis by gas chromatographic and mass spectrum techniques indicated 2-chlorobenzonitrile as the main product.

EXAMPLE 2

The procedure of Example 1 was repeated except that in place of 5.3 parts of 2-nitrobenzonitrile there was substituted 40 parts of 3-nitrobenzonitrile. The structure of the product 3-chlorobenzonitrile was confirmed by gas chromatography—mass spectrum and nuclear magnetic resonance analyses.

EXAMPLE 3

The procedure of Example 1 was repeated except that 4-nitrobenzonitrile (4.8 parts dissolved in 45 parts of chloroform) was substituted for 2-nitrobenzonitrile. The structure of the main product, 4-chlorobenzonitrile, was confirmed by gas chromatography—mass spectrum and nuclear magnetic resonance analyses.

EXAMPLE 4

Chlorine and 4-nitrobenzoyl chloride (as a solution of 4.4 parts in 37 parts of carbon tetrachloride) were introduced simultaneously (at a 10:1 mol ratio of $Cl_2$:nitrobenzoyl chloride) into a vapor phase reactor maintained at a temperature of 340° to 360° C. The reaction product was condensed and collected. Analysis by gas chromatographic—mass spectrum and nuclear magnetic resonance techniques confirmed the main product as 4-chlorobenzoyl chloride.

EXAMPLE 5

The procedure of Example 4 was repeated except that 3-nitrobenzoyl chloride (5.7 parts dissolved in 1.5 parts of carbon tetrachloride) was employed in place of 4-nitrobenzoyl chloride to yield a reaction product containing 3-chlorobenzoyl chloride as the major component. The structure of the 3-chlorobenzoyl chloride product was confirmed by gas chromatographic—mass spectrum and nuclear magnetic resonance analyses.

EXAMPLE 6

Chlorine and p-nitrotrifluoromethoxybenzene (10.7 parts) were fed simultaneously at a molar ratio of 3:1, $Cl_2$:organic reactant, into a vapor phase reactor maintained at 300° C. to 320° C. over a 30 minute period to yield 8.2 parts of p-chlorotrifluoromethoxybenzene (83% yield). The structure of the product was confirmed by gas chromatographic—mass spectrum and $F^{19}$ nuclear magnetic resonance analysis.

EXAMPLE 7

Chlorine and 3-fluoro-2-nitrophenyl isocyanate (4.1 parts dissolved in 24 parts of carbon tetrachloride) were introduced simultaneously ($Cl_2$:organic reactant, 10:1) into a vapor phase reactor maintained at about 310° C. Analysis of the reaction product by gas chromatographic mass spectrum and $F^{19}$ nuclear magnetic resonance techniques indicated 3-fluoro-2-chlorophenyl isocyanate as the major component.

EXAMPLE 8

In a continuous process, about 14 parts per hour of 2-fluoro-5-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 20 parts of 2-fluoro-5-nitrobenzotrifluoride and about 17.3 parts of chlorine gas had been passed through the reactor. Analysis of the reaction product indicated 16.7 parts of 5-chloro-2-fluorobenzotrifluoride, a yield of 89%. The structure of the product was confirmed by gas chromatography—mass spectrum $F^{19}$ and $C^{13}$ nuclear magnetic resonance analysis.

EXAMPLE 9

14.1 parts of 5-fluoro-2-nitrobenzotrifluoride vapors and 12.1 parts of chlorine gas were passed simultaneously, over a one hour period, through a vapor-phase reactor maintained at a temperature of about 320° to 380° C. The vaporized reaction product was condensed and collected. Analysis of the reaction product indicated 12.6 parts of 2-chloro-5-fluorobenzotrifluoride, a yield of 94%. The structure of the product was confirmed by gas chromatography—mass spectrum $F^{19}$ and $C^{13}$ nuclear magnetic resonance analysis.

EXAMPLE 10

In a continuous process, about 8 parts per hour of 4-fluoro-3-nitrobenzotrifluoride vapors and about 15 parts per hour of chlorine gas were passed simultaneously through a vapor phase reactor maintained at a temperature of about 320° C. and the reaction product vapors were condensed and collected. The process was continued until about 40 parts of 4-fluoro-3-nitrobenzotrifluoride had been passed through the reactor, yielding about 36.3 parts of 3-chloro-4-fluorobenzotrifluoride product. The structure of the product was confirmed by spectral analysis.

EXAMPLE 11 (A)

About 500 parts of aqueous nitric acid was added slowly, with stirring, to a reaction vessel containing about 400 parts of 3-chloro-4-fluorobenzotrifluoride. The temperature of the reaction mixture was maintained at about 40° C. during the addition, then raised to about 60° C. and maintained thereat for about 5 hours. The reaction mixture was allowed to settle. The aqueous layer was removed and the organic layer was washed twice with 500 parts of water, treated several times with a saturated solution of sodium bicarbonate, washed with water again, dried over anhydrous magnesium sulfate, and filtered. The filtrate was distilled at reduced pressure to yield 347 parts of 5-chloro-4-fluoro-2-nitrobenzotrifluoride.

EXAMPLE 11 (B)

In a continuous process, about 14 parts per hour of 5-chloro-4-fluoro-2-nitrobenzotrifluoride vapors and about 12 parts per hour of chlorine gas were passed simultaneously through a vapor phase reactor maintained at a temperature of about 320° to 380° C. The vaporized reaction product was condensed and collected. The process was continued until about 14.7 parts of 5-chloro-4-fluoro-2-nitrobenzotrifluoride had been added and 14.7 parts of 2,5-dichloro-4-fluorobenzotrifluoride product was collected. The structure of the product was confirmed by gas chromatography—mass spectrum, $F^{19}$ and $C^{13}$ nuclear magnetic resonance analysis.

The novel chlorofluorobenzotrifluorides of Examples 8—11 are particularly useful as intermediates for use in various organic syntheses based on nucleophilic aromatic substitution at the fluorine site. The following examples are typical of such syntheses.

EXAMPLE 12

Approximately 20 parts of 5-chloro-2-fluorobenzotrifluoride is reacted with 14 parts of powdered potassium hydroxide (85%) in dimethylsulfoxide solvent at a temperature of about 60°-70° C. for 12 to 16 hours to form 4-chloro-3-trifluoromethylphenolate. The reaction mixture is cooled, poured into iced water, and acidified with concentrated hydrochloric acid. The aqueous mixture is then extracted with methylene chloride and the organic layer dried and concentrated to recover 4-chloro-2-trifluoromethylphenol.

EXAMPLE 13

Approximately 20 parts of 2-chloro-5-fluorobenzotrifluoride is reacted with 14 parts of powdered potassium hydroxide (85%) in dimethylsulfoxide solvent at a temperature of about 60°-70° C. for 12 to 16 hours to form 4-chloro-3-trifluoromethylphenolate. The reaction mixture is cooled, poured into iced water, and acidified with concentrated hydrochloric acid. The aqueous mixture is then extracted with methylene chloride and the organic layer dried and concentrated to recover 4-chloro-3-trifluoromethylphenol. The concentrated product is mixed with ethanol solvent and reacted with hydrogen under basic conditions, in the presence of a noble catalyst to form m-hydroxybenzotrifluoride, a known and useful chemical intermediate.

EXAMPLE 14

Approximately 20 parts of 3-chloro-4-fluorobenzotrifluoride is reacted with 14 parts of powdered potassium hydroxide (85%) in dimethylsulfoxide solvent at a temperature of about 60°-70° C. for 12 to 16 hours to form 2-chloro-4-trifluoromethylphenolate. The reaction mixture is cooled, poured into iced water, and acidified with concentrated hydrochloric acid. The aqueous mixture is then extracted with methylene chloride and the organic layer dried and concentrated to recover 2-chloro-4-trifluoromethylphenol.

What is claimed is:

1. A process for the preparation of chloro-aromatic compounds of the formula

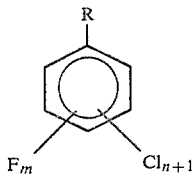

wherein R is $CF_3$, $OCF_3$, $OC_2F_5$, CN, NCO, or COCl, m is 0 or 1, and n is 0, 1 or 2, which comprises reacting chlorine with a nitro-aromatic compound of the formula

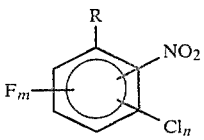

where R, m, and n are as defined above, in the vapor phase.

2. A process according to claim 1 wherein m is o, and n is o.

3. A process according to claim 1 wherein n is 1 and n is 0.

4. A process according to claim 1 wherein m is 0 and n is 1.

5. A process according to claim 1 wherein m is 1 and n is 1.

6. A process according to claims 1, 2, 3, 4, or 5 wherein the process is carried out at a temperature of about 250° to about 450° Celsius.

7. A process according to claim 1 wherein a chlorobenzotrifluoride of the formula

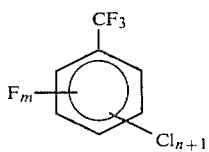

where m is 0 or 1 and n is 0 or 1, is prepared by the vapor phase chloro-denitration reaction of a nitro-benzotrifluoride compound of the formula

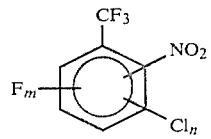

where m and n are as defined above, with chlorine.

8. A process according to claim 7 wherein m is 0 and n is 0.

9. A process according to claim 7 wherein m is 1 and n is 0.

10. A process according to claim 7 wherein m is 0 and n is 1.

11. A process according to claim 7 wherein m is 1 and n is 1.

12. A process according to claim 7 wherein 3-chloro-4-fluorobenzotrifluoride is prepared by the vapor phase chloro-denitration reaction of 4-fluoro-3-nitro-benzotrifluoride with chlorine.

13. A process according to claim 7 wherein 2-chloro-5-fluorobenzotrifluoride is prepared by the vapor phase chloro-denitration reaction of 5-fluoro-2-nitrobenzotrifluoride with chlorine.

14. A process according to claim 7 wherein 5-chloro-2-fluorobenzotrifluoride is prepared by the vapor phase chloro-denitration reaction of 2-fluoro-5-nitrobenzotrifluoride with chlorine.

15. A process according to claim 7 wherein 2,5-dichloro-4-fluorobenzotrifluoride is prepared by the vapor phase chloro-denitration reaction of 5-chloro-4-fluoro-2-nitrobenzotrifluoride with chlorine.

16. A process according to claims 7, 8, 9, 10, 11, 12, 13, 14 or 15 wherein the reaction is carried out at a temperature of about 290° to about 410° Celsius.

17. A process according to claim 1 wherein a chlorobenzonitrile of the formula

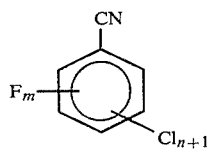

where m is 0 or 1 and n is 0 or 1, is prepared by the vapor phase chloro-denitration reaction of a nitro-benzonitrile compound of the formula

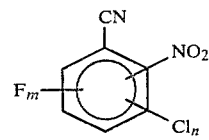

where m and n are as defined above, with chlorine.

18. A process according to claim 17 wherein m is 0 and n is 0.

19. A process according to claim 17 wherein m is 1 and n is 0.

20. A process according to claim 17 wherein m is 0 and n is 1.

21. A process according to claim 17 wherein m is 1 and n is 1.

22. A process according to claim 17 wherein 2-chlorobenzonitrile is prepared by the vapor phase chloro-denitration reaction of 2-nitrobenzonitrile with chlorine.

23. A process according to claim 17 wherein 3-chlorobenzonitrile is prepared by the vapor phase chloro-denitration reaction of 3-nitrobenzonitrile with chlorine.

24. A process according to claim 17 wherein 4-chlorobenzonitrile is prepared by vapor phase chloro-denitration reaction of 4-nitrobenzonitrile with chlorine.

25. A process according to claims 17, 18, 19, 20, 21, 22, 23, or 24 wherein the reaction is carried out at a temperature of about 290° to about 410° Celsius.

26. A process according to claim 1 wherein a chlorobenzoyl chloride of the formula

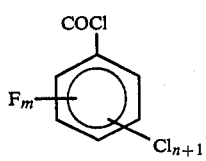

where m is 0 or 1 and n is 0 or 1, is prepared by the vapor phase chloro-denitration reaction of a nitrobenzoyl chloride of the formula

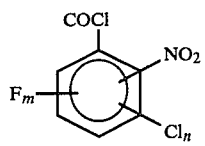

where m and n are as defined above, with chlorine.

27. A process according to claim 26 wherein m is 0 and n is 0.

28. A process according to claim 26 wherein m is 1 and n is 0.

29. A process according to claim 26 wherein n is 0 and n is 1.

30. A process according to claim 26 wherein m is 1 and n is 1.

31. A process according to claim 26 wherein 4-chlorobenzoyl chloride is prepared by the vapor phase chloro-denitration reaction of 4-nitrobenzoyl chloride with chlorine.

32. A process according to claim 26 wherein 3-chlorobenzoyl chloride is prepared by the vapor phase chloro-denitration reaction of 3-nitrobenzoyl chloride with chlorine.

33. A process according to claims 26, 27, 28, 29, 30, 31, or 32 wherein the reaction is carried out at a temperature of about 290° to about 410° Celsius.

34. A process according to claim 1 wherein a chlorophenyl isocyanate of the formula

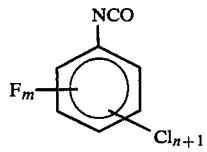

where m is 0 or 1 and n is 0 or 1, is prepared by the vapor phase chloro-denitration reaction of a nitrophenyl isocyanate of the formula

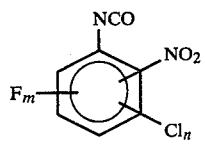

where m and n are as defined above, with chlorine.

35. A process according to claim 34 wherein m is 0 and n is 0.

36. A process according to claim 34 wherein m is 1 and n is 0.

37. A process according to claim 34 wherein m is 0 and n is 1.

38. A process according to claim 34 wherein m is 1 and n is 1.

39. A process according to claim 34 wherein 3-fluoro-2-chlorophenyl isocyanate is prepared by the vapor phase chloro-denitration reaction of 3-fluoro-2-nitrophenyl isocyanate with chlorine.

40. A process according to claims 34, 35, 36, 37, 38 or 39, wherein the reaction is carried out at a temperature of about 290° to about 410° Celsius.

41. A process according to claim 1 wherein a chloropentafluoroethoxybenzene of the formula

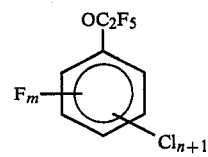

where m is 0 or 1 and n is 0 or 1, is prepared by the vapor phase chloro-denitration reaction of a nitro-pentafluoroethoxybenzene of the formula

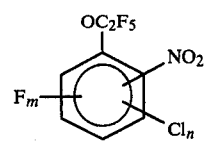

where m and n are as defined above, with chlorine.

42. A process according to claim 41 wherein m is 0 and n is 0.

43. A process according to claim 41 wherein m is 1 and n is 0.

44. A process according to claim 41 wherein m is 0 and n is 1.

45. A process according to claim 41 wherein m is 1 and n is 1.

46. A process according to claims 41, 42, 43, 44, or 45, wherein the reaction is carried out at a temperature of about 290° to about 410° Celsius.

47. A process according to claim 1 wherein a chloro-trifluoromethoxybenzene of the formula

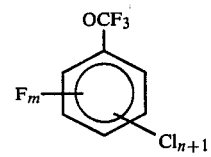

where m is 0 or 1 and n is 0 or 1, is prepared by the vapor phase chloro-denitration reaction of a nitro-fluoromethoxybenzene of the formula

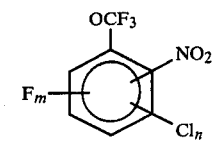

where m and n are as defined above, with chlorine.

48. A process according to claim 47 wherein m is 0 and n is 0.

49. A process according to claim 47 wherein m is 1 and n is 0.

50. A process according to claim 47 wherein m is 0 and n is 1.

51. A process according to claim 47 wherein m is 1 and n is 1.

52. A process according to claim 47 wherein 4-chlorotrifluoromethoxybenzene is prepared by the vapor phase chloro-denitration reaction of 4-nitrotrifluoromethoxybenzene with chlorine.

53. A process according to claims 47, 48, 49, 50, 51, or 52 wherein the reaction is carried out at a temperature of about 290° to about 410° Celsius.

* * * * *

REEXAMINATION CERTIFICATE (1130th)
United States Patent
Tang et al.

[11] B1 4,470,930
[45] Certificate Issued  Sep. 26, 1989

[54] PREPARATION OF NUCLEAR CHLORINATED AROMATIC COMPOUNDS

[75] Inventors: David Y. Tang, Amherst; Byron R. Cotter, Grand Island, both of N.Y.; Frederick J. Goetz, Santa Ana, Calif.

[73] Assignee: Occidental Chemical Corporation, Niagara Falls, N.Y.

Reexamination Request:
No. 90/001,311, Aug. 24, 1987

Reexamination Certificate for:
Patent No.: 4,470,930
Issued: Sep. 11, 1984
Appl. No.: 347,390
Filed: Feb. 9, 1982

[51] Int. Cl.$^4$ ............................................ C07C 121/52
[52] U.S. Cl. .................... 558/425; 560/349; 568/656; 570/127
[58] Field of Search .................. 260/544 D; 558/425; 560/349; 568/656; 570/127

[56] References Cited

FOREIGN PATENT DOCUMENTS
2503736  8/1976  Fed. Rep. of Germany .

OTHER PUBLICATIONS

I. W. Engelsma and E. C. Kooyman, Recueil, 80, 537–544 (1961); "The Halogenation of Aromatics"–Part VI, Types of Reactions Occurring in the Gas–Phase Halogenation of Benzene Derivatives.

R. J. Albers and E. C. Kooyman, Recueil, 83, 930–936 (1964); "The Halogenation of Aromatics"–Part IX, Vapor-Phase Chlorination and Bromination of Benzotrifluoride.

E. C. Kooyman, Free Radical Halogenations in the Gas Phase, Advances in Chemistry, vol. I, 137–153 (1965); "Vapor Phase Halogenation of Aromatic Compounds".

N. N. Vorozhtsov et al., Zhurnal Obshehei Khimii, 31, 1222–1226 (1961); "Aromatic Fluoro Derivatives IV, Replacement of Nitro Group by Chlorine in Nitrohalo Derivatives of Benzene".

W. A. Sheppard, J. Am. Chem. Soc., 85, 1314–1318 (1963); "The Effect of Fluorine Substitution on the Electronic Properties of Alkoxy, Alkylthio and Alkylsulfonyl Groups".

E. Klauke et al., Synthesis, 5, 376–377 (1978); "Manufacture of 2-(mono-, di- and trichloromethyl)–phenyl–isocyanates".

Primary Examiner—Anton H. Sutto

[57] ABSTRACT

Chloro-aromatic compounds of the formula

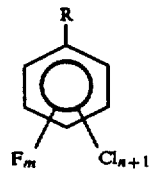

wherein R is $CF_3$, $OCF_3$, $OC_2F_5$, CN, NCO, or COCl, m is 0 or 1, and n is 0 or 1 are prepared by the vapor phase chloro-denitration reaction of a chlorinating agent with a nitro-aromatic compound of the formula

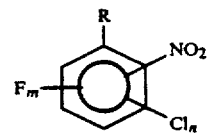

where R, m, and n are as defined above.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-53 are cancelled.